(12) United States Patent
van den Honert et al.

(10) Patent No.: US 8,391,993 B2
(45) Date of Patent: Mar. 5, 2013

(54) USING INTERACTION TO MEASURE NEURAL EXCITATION

(75) Inventors: Christoper van den Honert, Boulder, CO (US); Zachary Smith, Englewood, CO (US); Christopher J. Long, Centennial, CO (US); Daniel M. Lisogurski, Boulder, CO (US); Robert P. Carlyon, Cambridge (GB)

(73) Assignee: Cochlear Limited, Macquarie University, NSW (AU)

(*) Notice: Subject to any disclaimer, the term of this patent is extended or adjusted under 35 U.S.C. 154(b) by 1243 days.

(21) Appl. No.: 12/172,850

(22) Filed: Jul. 14, 2008

(65) Prior Publication Data

US 2009/0132006 A1 May 21, 2009

Related U.S. Application Data

(60) Provisional application No. 60/949,682, filed on Jul. 13, 2007, provisional application No. 60/949,647, filed on Jul. 13, 2007.

(51) Int. Cl.
*A61F 11/04* (2006.01)

(52) U.S. Cl. ............ 607/115; 607/1; 607/2; 607/55; 607/56; 607/57; 607/136; 607/137

(58) Field of Classification Search .......... 607/1–2, 607/55–57, 115, 136–137
See application file for complete search history.

(56) References Cited

U.S. PATENT DOCUMENTS

| | | | |
|---|---|---|---|
| 4,284,856 A | 8/1981 | Hochmair et al. | |
| 4,357,497 A | 11/1982 | Hochmair et al. | |
| 4,495,384 A | 1/1985 | Scott et al. | |
| 4,535,785 A | 8/1985 | van den Honert et al. | |
| 4,947,844 A | 8/1990 | McDermott | |
| 5,983,139 A | 11/1999 | Zierhofer | |
| 6,074,422 A | 6/2000 | Berrang et al. | |
| 6,594,525 B1 | 7/2003 | Zierhofer et al. | |
| 6,600,955 B1 | 7/2003 | Zierhofer et al. | |
| 6,751,505 B1 | 6/2004 | Van Den Honert et al. | |
| 6,915,166 B1 | 7/2005 | Stecker et al. | |
| 7,043,303 B1 | 5/2006 | Overstreet | |
| 7,103,417 B1 | 9/2006 | Segel et al. | |
| 7,110,821 B1 | 9/2006 | Ross | |
| 7,136,706 B1 | 11/2006 | Voelkel | |
| 7,149,583 B1 | 12/2006 | Litvak | |
| 7,174,215 B2 | 2/2007 | Bradley | |
| 7,206,640 B1 | 4/2007 | Overstreet | |
| 7,209,789 B2 | 4/2007 | Zierhofer et al. | |
| 7,231,257 B2 | 6/2007 | McDermott et al. | |
| 7,283,876 B2 | 10/2007 | Zierhofer et al. | |

(Continued)

FOREIGN PATENT DOCUMENTS

WO 2009010870 1/2009
WO 2009013616 1/2009

OTHER PUBLICATIONS

Terry A. Zwolan, "Electrode discrimination and speech recognition in postlingually deafened adult cochlear implant subjects", J. Acoust. Soc. Am. 102(5), Dec. 1997 (13 pages).

(Continued)

*Primary Examiner* — Deborah Malamud
(74) *Attorney, Agent, or Firm* — Kilpatrick, Townsend & Stockton, LLP.

(57) ABSTRACT

Assessment of neuron excitation is implemented by quantifying the interaction between focused and unfocused stimulation applied to a cochlear array. By applying focused and unfocused stimulation to the electrode array and comparing the difference in the responses to the two types of stimulation the interaction may be determined. The magnitude of the interaction may be related to neural excitation and using this data a neural excitation profile may be determined.

25 Claims, 9 Drawing Sheets

U.S. PATENT DOCUMENTS

| | | | |
|---|---|---|---|
| 7,292,891 | B2 | 11/2007 | Hartley et al. |
| 2003/0163060 | A1 | 8/2003 | Maddess et al. |
| 2006/0052841 | A1 | 3/2006 | Daly et al. |
| 2006/0247735 | A1 | 11/2006 | Honert |
| 2006/0265061 | A1 | 11/2006 | Kwon et al. |
| 2007/0129771 | A1 | 6/2007 | Kurtz et al. |
| 2009/0132005 | A1 | 5/2009 | van den Honert et al. |
| 2009/0132006 | A1 | 5/2009 | van den Honert et al. |

OTHER PUBLICATIONS

International Searching Authority, "International Search Report," issued in connection with International Patent Application No. PCT/IB2008/002177, mailed on Aug. 31, 2009 (3 pages).

International Searching Authority, "Written Opinion," issued in connection with International Patent Application No. PCT/IB2008/002177, mailed on Aug. 31, 2009 (6 pages).

The International Bureau of WIPO, "International Preliminary Report on Patentability," issued in connection with International Patent Application No. PCT/IB2008/002177, on Jan. 19, 2010 (7 pages).

International Searching Authority, "International Search Report," issued in connection with International Patent Application No. PCT/IB2008/002178, mailed on Jul. 24, 2009 (1 page).

International Searching Authority, "Written Opinion," issued in connection with International Patent Application No. PCT/IB2008/002178, mailed on Jul. 24, 2009 (4 pages).

The International Bureau of WIPO, "International Preliminary Report on Patentability," issued in connection with International Patent Application No. PCT/IB2008/002178, on Jan. 19, 2010 (5 pages).

Bierer et al., "Cortical Responses to Cochlear Implant Stimulation: Channel Interactions," on Nov. 12, 2002, published in pp. 32-48, vol. 5, No. 1, Journal of the Association for Research in Otolaryngology, Mar. 2004 (published online on Oct. 20, 2003) (17 pages).

Bierer, Julie Arenberg, "Threshold and Channel Interaction in Cochlear Implant Users: Evaluation of the Tripolar Electrode Configuration," on May 15, 2006, published in pp. 1642-1653, vol. 121, No. 3, The Journal of the Acoustical Society of America, Mar. 2007 (12 pages).

Busby et al., "Pitch Perception for Different Modes of Stimulation Using the Cochlear Multiple-Electrode Prosthesis," on Apr. 26, 1993, published in pp. 2658-2669, Vo. 95, No. 1, The Journal of the Acoustical Society of America, May 1994 (12 pages).

Cohen et al., "Spatial Spread of Neural Excitation in Cochlear Implant Recipients: Comparison of Improved ECAP Method and Psychophysical Forward Masking," on Oct. 31, 2002, published in pp. 72-87, vol. 179, Hearing Research, May 2003 (16 pages).

Dingemanse et al., "Psychophysical Assessment of Spatial Spread of Excitation in Electrical Hearing with Single and Dual Electrode Contact Maskers," pp. 645-657, vol. 27, No. 6, Ear and Hearing, Dec. 2006 (13 pages).

Hall, Robert D., "Estimation of Surviving Spiral Ganglion Cells in the Deaf Rat Using the Electrically Evoked Auditory Brainstem Response," on Aug. 24, 1989, published in pp. 123-136, vol. 45, Hearing Research, 1990 (14 pages).

Hall, Robert D., "Estimation of Surviving Spiral Ganglion Cells in the Deaf Rat Using the Electrically Evoked Auditory Brainstem Response," on Aug. 24, 1989, published in pp. 155-168, vol. 49, Hearing Research, Nov. 1990 (14 pages).

Honert et al., "Focused Intracochlear Electric Stimulation with Phased Array Channels," Aug. 1, 2006, published in pp. 3703-3716, vol. 121, No. 6, The Journal of the Acoustical Society of America, Jun. 2007 (14 pages).

Honert et al., "Single Fiber Mapping of Spatial Excitation Patterns in the Electrically Stimulated Auditory Nerve," on Dec. 4, 1986, published in pp. 195-206, vol. 29, Hearing Research, 1987 (12 pages).

Kwon et al., "Effect of Electrode Configuration on Psychophysical Forward Masking in Cochlear Implant Listeners," Jul. 11, 2005, pp. 2994-3002, vol. 119, No. 5, The Journal of the Acoustical Society of America, May 2006 (9 pages).

Bryan E. Pfingst et al., "Across-Site Variation in Detection Thresholds and Maximum Comfortable Loudness Levels for Cochlear Implants", JARO 5: 11-24 (2004) (14 pages).

Paul J. Abbas et al., "Summary of Results Using the Nucleus CI24M Implant to Record the Electrically Evoked Compound Action Potential", Ear and Hearing, vol. 20, No. 1, pp. 45-59, Feb. 1999 (15 pages).

Monita Chatterjee et al., "Effects of Stimulation Mode, Level and Location on Forward-Masked Excitation Patterns in Cochlear Implant Patients", JARO 7: 15-25 (2006) (11 pages).

Extended European Search Report for European Application No. 08789109.9 dated Feb. 7, 2012 (12 pages).

Extended European Search Report for European Application No. 08826588.9 dated Feb. 9, 2012 (11 pages).

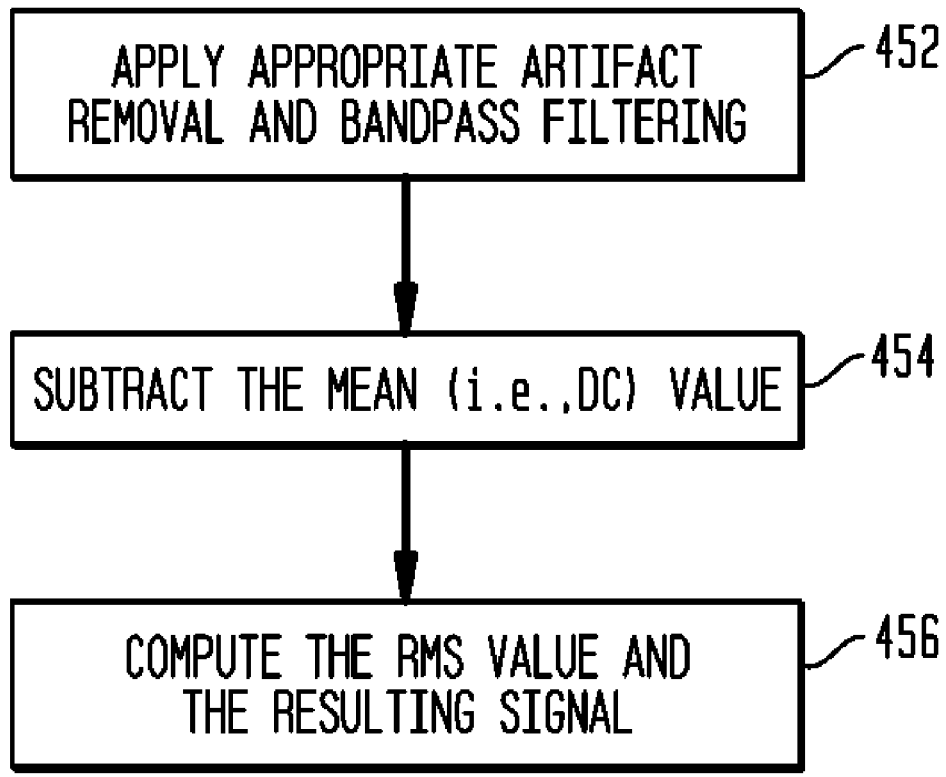

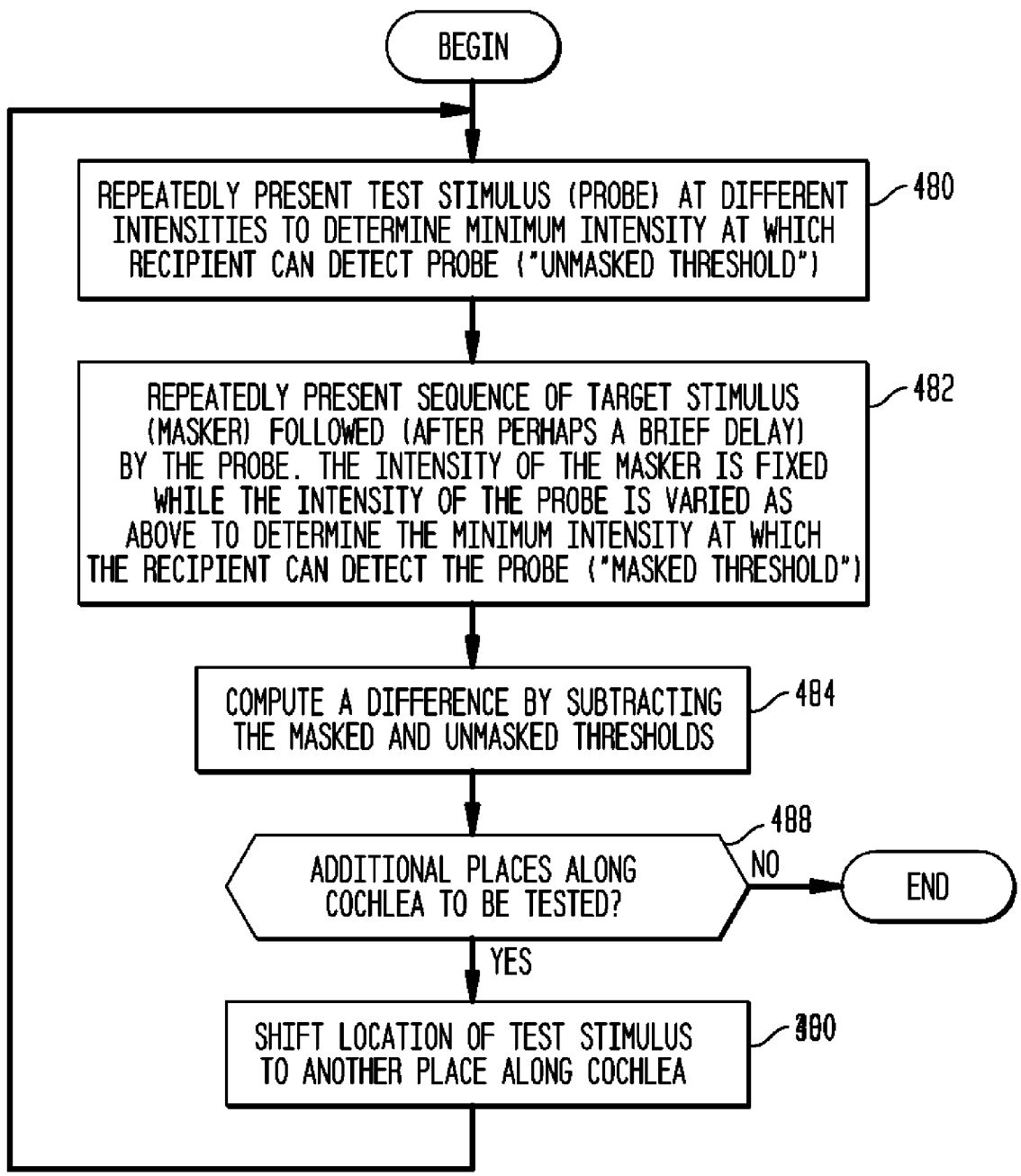

UNITED STATES PATENT

USING INTERACTION TO MEASURE NEURAL EXCITATION

CROSS-REFERENCE TO RELATED APPLICATIONS

This application claims the benefit of U.S. Provisional Application No. 60/949,682, entitled "USE OF FOCUSED STIMULI TO MEASURE A NEURAL EXCITATION PROFILE WITHIN THE COCHLEA," filed Jul. 13, 2007 and U.S. Provisional Application No. 60/949,647 entitled "USE OF FOCUSED STIMULI TO MEASURE A NEURAL EXCITATION PROFILE WITHIN THE COCHLEA", filed Jul. 13, 2007 which are both hereby incorporated by reference herein. This application is related to U.S. Utility patent application entitled "ASSESSING NEURAL SURVIVAL" filed on Jul. 14, 2008, which is hereby incorporated by reference herein.

BACKGROUND

1. Field of the Invention

The present invention relates generally to assessing neural excitation, and more particularly, to assessing neural excitation associated with an implanted electrode array.

2. Related Art

Prosthetic implants systems are now being used to directly deliver electrical stimulation to auditory nerve fibers of a recipient's cochlea to cause the recipient's brain to perceive a hearing sensation resembling the natural hearing sensitivity normally delivered to the auditory nerve. One form of such a prosthetic hearing implant system is a Cochlear implant. An example of a cochlear implant system is described in US Patent Publication 2006/0247735 (the contents of which are here and incorporated by this reference).

The relationship between the hearing sensation afforded to the recipient of the cochlear implant and the excitation of the electrodes in the electrode array varies from recipient to recipient. Consequently it is important to be able to determine the neural excitation profile of the electrode array. In particular the locus of excitation for each electrode in the cochlea array is typically unknown. Some electrodes may stimulate locally, others more broadly. In some cases the stimulus may jump across turns and excite at two places.

SUMMARY

In accordance with one aspect of the present invention, a method of assessing neural excitation using interaction between two stimuli, wherein both stimuli are applied by at least one electrode of an electrode array is provided. The method comprises: applying a first stimulus; capturing a response to the first stimulus; applying a second stimulus in timed relation to application of the first stimulus; capturing a response to the second stimulus; and determining neural excitation from the captured responses, wherein at least one of the first and second stimulus is focused.

In accordance with another aspect of the present invention, a method of assessing neural excitation by a given stimulus by measuring a response to interaction of two stimuli, including the given stimulus, each stimulus applied to at least one electrode in an array is provided. The method comprises: applying a first stimulus to at least one electrode of the array; capturing a first response to application of a first stimulus; applying a second stimulus to at least one electrode of the array; capturing a second response to application of a second stimulus; capturing a third response to a sequence of the second stimulus followed, after a given delay, by the first stimulus; determining a computed response by summing the first and second responses, temporally adjusted to exhibit a delay equivalent to the given delay; and determining a difference response by obtaining a difference between the computed response and the third response.

BRIEF DESCRIPTION OF THE DRAWINGS

The present invention will now be further described in the following portions of this application in conjunction with the attached drawings in which like reference characters identify identical apparatus and in which:

FIG. 4B is a detail of step 412 of FIG. 4A;

FIG. 4C is a flow diagram of another embodiment of the invention;

DETAILED DESCRIPTION

Figure 1:
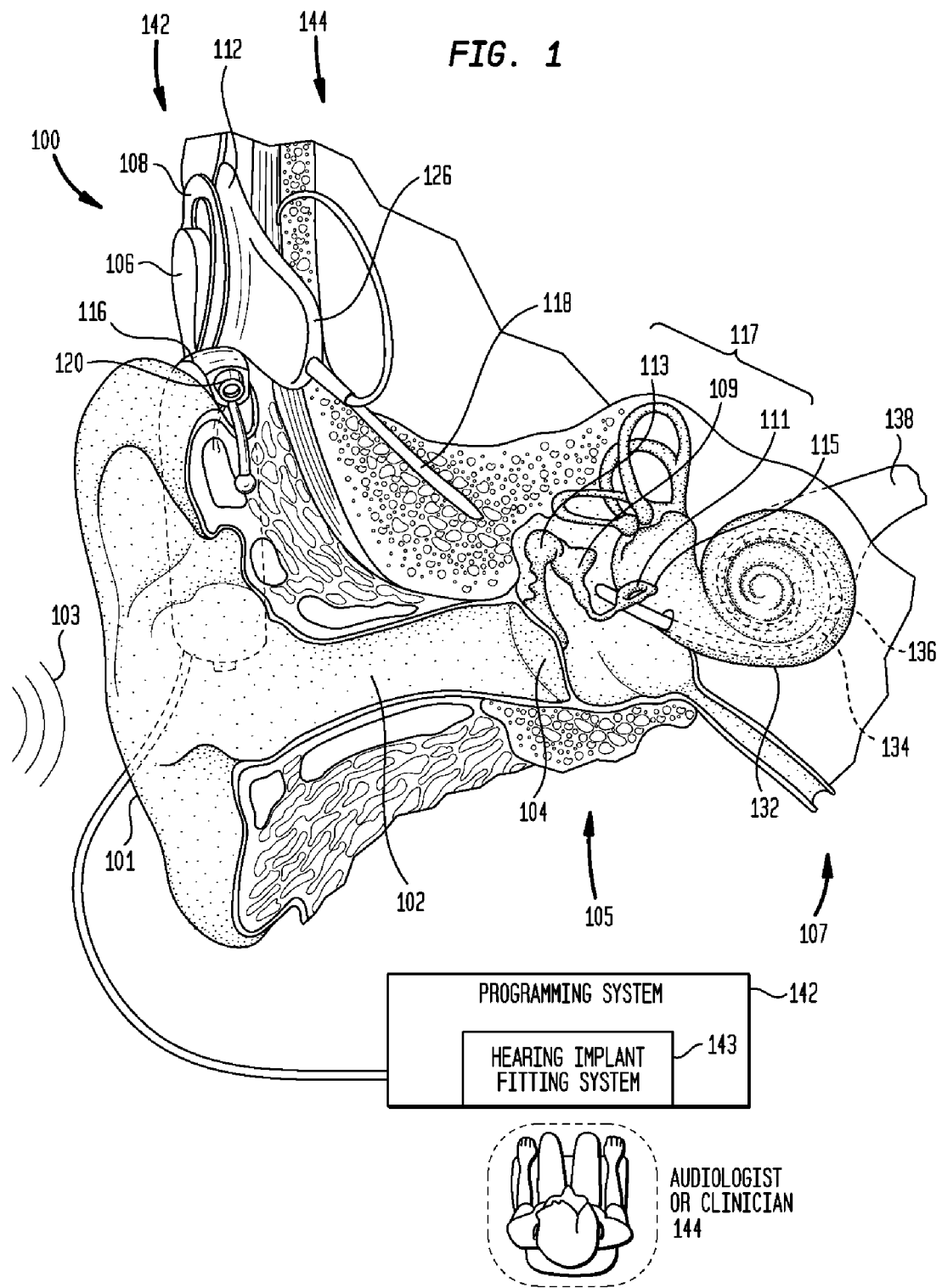
FIG. 1 schematically shows a conventional cochlear implant in place in a recipient's ear and associated apparatus including a programming system 142 available for operation by an audiologist or clinician.

Aspects of the present invention assess neural excitation and/or determine an excitation profile by using the interaction between the responses to two stimuli. One of the two stimuli is a stimulus having an unknown locus of neural excitation; i.e., the excitation which is to be determined, referred to herein as the target stimulus. The second stimulus is a focused stimulus which excites neurons over a spatial range which is at least narrower than the target stimulus, referred to herein as the test stimulus. The location of the test stimulus is systematically varied along the longitudinal tonotopic dimension of the cochlea. At each test location the interaction between the target and test stimulus is captured and/or measured. In one embodiment, interaction is determined by first capturing the response to each of the test and target stimulus separately and then capturing the response to application of the test and target stimulus applied in sequence. A difference is obtained between the response to the sequential application and the sum of the responses to the separate stimulations. The degree of interaction is based on this difference. The degree of interaction is a measure of the neural excitation by the target stimulus at the place where the testing stimulus is applied. Concatenating the degree of interaction across the entire electrode array produces an excitation profile. The details of interaction may give insight into the affected spread of the target stimulus for the individual recipient.

There are several techniques which may be employed for focusing the test stimulus. One preferred embodiment focuses a test stimulus using "phased array" (PA) channel as described in patent publication 2006/0247735. The phased array channel exploits constructive and destructive interference across fields from all available electrodes to create non-zero voltages within the scala tympani at one and only one electrode contact place.

In a particular embodiment, the interaction between the target and test stimuli may be measured as follows: applying a first stimulus; capturing a response to the first stimulus; applying a second stimulus; capturing a response to the second stimulus; applying a sequence of the second stimulus followed after a brief delay by the first stimulus; capturing a response to the foregoing sequence; determining a computed response by summing the first and second responses temporally adjusted to exhibit a delay equivalent to the delay between the stimuli in the sequence; computing a difference response by obtaining the difference between the computed response and the third response.

Preferably the first or second stimulus is focused. In the preferred embodiment the first stimulus is the target stimulus and the second stimulus, the test stimulus, is focused. The response may be an evoked potential such as the Electrical Auditory Brainstem Response (EABR). Alternatively, the response may be a compound action potential or a perceptual response from the recipient.

In order to employ the difference response for assessing neural excitation, the difference response is quantified by first determining a mean, producing a result by subtracting the mean from the difference response and computing a root mean square value (rms) of the result. In quantifying we use the rms value to quantify the difference responses. Preferably, before determining the mean, the difference response is subjected to appropriate artifact removal and bandpass filtering. The method briefly described above is iteratively repeated with a test stimulus focused at different locations in the array. Each interaction produces an rms value corresponding to the interaction result at the location at which the test stimulus was focused. After a sufficient number of iterations to cover all the locations in the electrode array, a profile is produced with a scalar of value for each different location in the array.

In another aspect the invention is applied based on perception of a recipient. In this aspect too there are two stimuli which are employed. A first stimulus, referred to as a probe, is initially presented at an imperceptible intensity. The intensity is increased until the stimulus becomes perceptible. The intensity at which the probe becomes perceptible is referred to as the unmasked threshold. Thereafter a sequence of two stimuli is presented. The first stimulus in the sequence is termed a masker. The masker is presented at a judiciously chosen intensity. The masker is followed (either immediately or after a predetermined delay) by the probe. The probe in the sequence is initially presented at an imperceptible intensity. The presentation of the sequence is repeated as the intensity of the probe is increased until the probe is again perceptible. This intensity is termed the masked threshold. A difference between the masked and unmasked threshold is computed. The difference is representative of an interaction between the stimuli. One of the two stimuli may be and preferably is focused. In some embodiments the probe is focused. In those embodiments the foregoing test is repeated with the probe focused at different locations (electrodes) in the electrode array. In this way an excitation profile is created based on the interaction value which has been determined for each location of the focused probe. The focusing may use constructive and destructive interference and preferably is implemented with a phased array. The delay may be non-existent (the probe follows the masker with no delay) or it may be a small delay such as 20 ms. The delay may be selected from a range of zero to about 100 ms.

Still other aspects of the invention include a computer readable medium supporting a sequence of instructions which, when executed in a suitable computer implement a method as described above.

FIG. 1 is a perspective view of an exemplary stimulating prosthetic hearing implant, comprising Cochlear implant 100. The present invention may be applied to glean important information about the characteristics of the implant as will be described. The relevant components of outer ear 101, middle ear 105 and inner ear 107 are described next below, followed by a description of Cochlear implant 100.

An acoustic pressure or sound wave 103 is collected by outer ear 101 (that is, the auricle) and channeled into and through ear canal 102. Disposed across the distal end of ear canal 102 is a tympanic membrane 104 which vibrates in response to acoustic wave 103. This vibration is coupled to oval window or fenestra ovalis 115 through three bones of middle ear 105, collectively referred to as the ossicles 137 and comprising the malleus 133, the incus 109 and the stapes 133. Bones 133, 109 and 133 of middle ear 105 serve to filter and amplify acoustic wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear prosthesis 100 comprises external component assembly 142 which is directly or indirectly attached to the body of the recipient, and an internal component assembly 144 which is temporarily or permanently implanted in the recipient.

External assembly 142 typically comprises a sound transducer 120 for detecting sound, and for generating an electrical audio signal, typically an analog audio signal. In this illustrative embodiment, sound transducer 120 is a microphone. In alternative embodiments, sound transducer 120 may comprise, for example, more than one microphone, one or more a telecoil induction pickup coils or other device now or later developed that may detect sound and generate electrical signals representative of such sound.

External assembly 142 also comprises a speech processing unit 116, a power source (not shown), and an external transmitter unit 106. External transmitter unit 106 comprises an external coil 108 and, preferably, a magnet (not shown) secured directly or indirectly to the external coil 108.

Speech processing unit 116 processes the output of microphone 120 that is positioned, in the depicted embodiment, by outer ear 101 of the recipient. Speech processing unit 116 generates coded signals, referred to herein as a stimulation data signals, which are provided to external transmitter unit 106 via a cable (not shown). Speech processing unit 116 is, in this illustration, constructed and arranged so that it may fit behind outer ear 101. Alternative versions may be worn on the body or it may be possible to provide a fully implantable system which incorporates the speech processor and/or microphone into the internal component assembly 144.

Internal components 144 comprise an internal receiver unit 132, a stimulator unit 126 and an electrode assembly 138. Internal receiver unit 112 comprises an internal transcutaneous transfer coil (not shown), and preferably, a magnet (also not shown) fixed relative to the internal coil. Internal receiver unit 112 and stimulator unit 126 are hermetically sealed within a biocompatible housing. The internal coil receives power and data from external coil 108, as noted above. A cable or lead of electrode assembly 118 extends from stimulator unit 126 to cochlea 132 and terminates in an array 134 of electrodes 136. Signals generated by stimulator unit 126 are applied by electrodes 136 to cochlea 132, thereby stimulating the auditory nerve 138.

In one embodiment, external coil 108 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 112 may be positioned in a recess of the temporal bone adjacent to outer ear 101 of the recipient.

It should be appreciated that, as noted elsewhere herein, embodiments of the present invention may be implemented in stimulating prosthetic hearing implants other than Cochlear implant 100. For example, while Cochlear implant 100 is described as having external components, in alternative embodiments, Cochlear implant 100 may be a totally implantable prosthesis. In one exemplary implementation, for example, sound processing unit 116, including microphone 120, a sound processor and/or a power supply may be implemented as one or more implantable components.

As shown in FIG. 1, Cochlear implant 100 is further configured to interoperate with an external processor 142 such as a personal computer, workstation or the like, implementing a hearing implant fitting system.

Stimulation strategies have employed unipolar and bipolar stimulation, where current flows from one electrode to a ground or common electrode or to another nearby electrode. The change from unipolar to bipolar stimulation reveals modest spatial sharpening.

Other stimulation strategies include tripolar or quadrupolar electrode configurations as a means for narrowing the stimulus area of an electrode. Certain embodiments of such configurations are described in Jolly C N, Spelman F A, Clopton B M, "Quadrupolar stimulation for Cochlear prostheses: modeling and experimental data," IEEE Trans. Biomed. Eng. 43(8):857-865 (3996); Clopton & Spelman, "Electrode configuration and spread of neural excitation: compartmental models of spiral ganglion cells," Ann. Otol. Rhinol. Laryngol. 366:335-338 (Suppl. 3995); Miyoshi, et al., "Proposal of a new auditory nerve stimulation method for cochlear prosthesis," Artif Organs 20:943-946 (3996); Kral, et al., "Spatial resolution of cochlear implants: the electrical field and excitation of auditory afferents," Hear Res. 323:33-28 (3998); Townshend, et al., "Pitch perception by cochlear implant subjects," J. Acoust. Soc. Am. 82(3):306-335 (3987), the entire contents and disclosures of which are hereby incorporated by reference herein. The above and other prior art tripolar/quadrupolar approaches utilize fixed weights based upon mathematical models, or physiological measurements, and do not contemplate consideration of the individual recipients.

Figure 2:
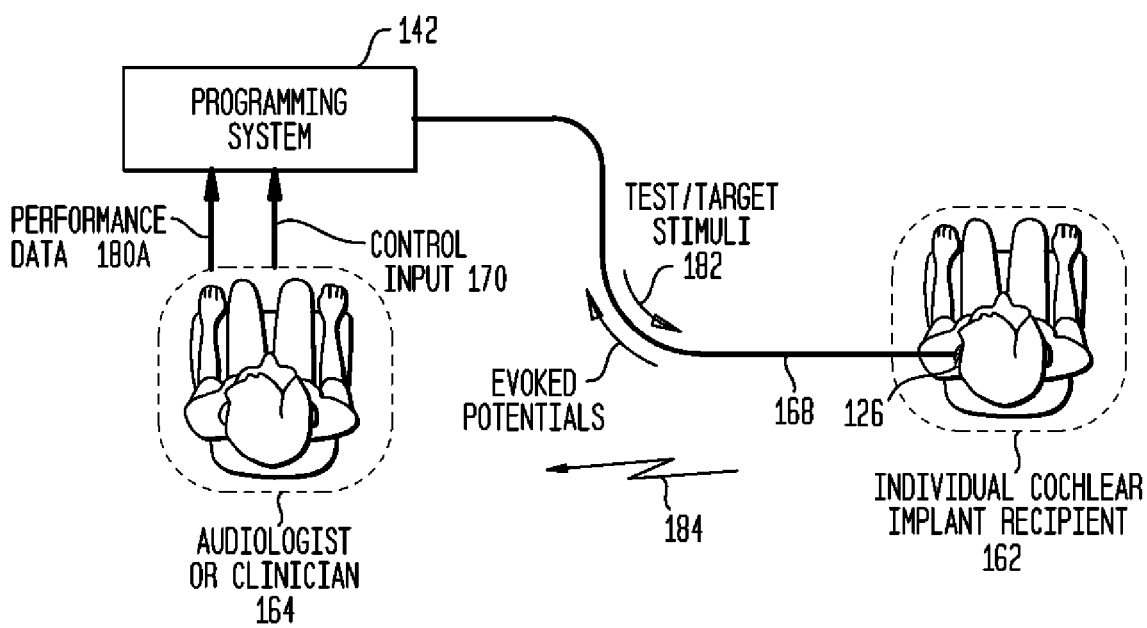
FIG. 2 is a more detailed view of the equipment operated by the audiologist and its relation to the recipient illustrating the controls available to the audiologist and the signal paths from/to programming system and the implant.

FIG. 2 is a schematic illustration of application of the invention involving an audiologist 164 and a recipient 162. Preparatory to executing the method of the invention, the recipient 162 has received an implant 100, such as that illustrated in FIG. 1. Signals to the implant 100 are generated by the programming system 142. The programming unit 142 also receives signals (Evoked Potentials) from the implant 100 via the path 168. The audiologist 164, through the control input 170 controls the programming system 142 so as to apply appropriate tests/target stimuli to the implant 100 via the path 168. The programming system 142, as will be described, is arranged to capture or record the responses on the array in response to the various stimuli. In other embodiments the responses may be captured or recorded from electrodes located elsewhere such as EABR which employs signals recorded from the scalp.

One embodiment of the invention relies on a response which comprises the evoked potential. However, another embodiment of the invention employs responses generated by the recipient's perception. Those responses may be audibilized by the recipient or manifested by pressing a button or touching a screen. The capture and recording of these and other similar responses are represented in FIG. 2 as the arrow 184. In the embodiments of the invention in which electrical signals are the responses which are captured or measured, the programming system 142 captures and/or records those signals. In embodiments in which the recipient's perception is the response, those may be also implemented as electrical signals which may be captured as other electrical signals or the perception may be relayed to the clinician 164 who may then input information received from the recipient's perception.

A first embodiment of the invention will now be described in connection with FIGS. 4A, 4B, 5A-5E and 6.

Figure 4A:
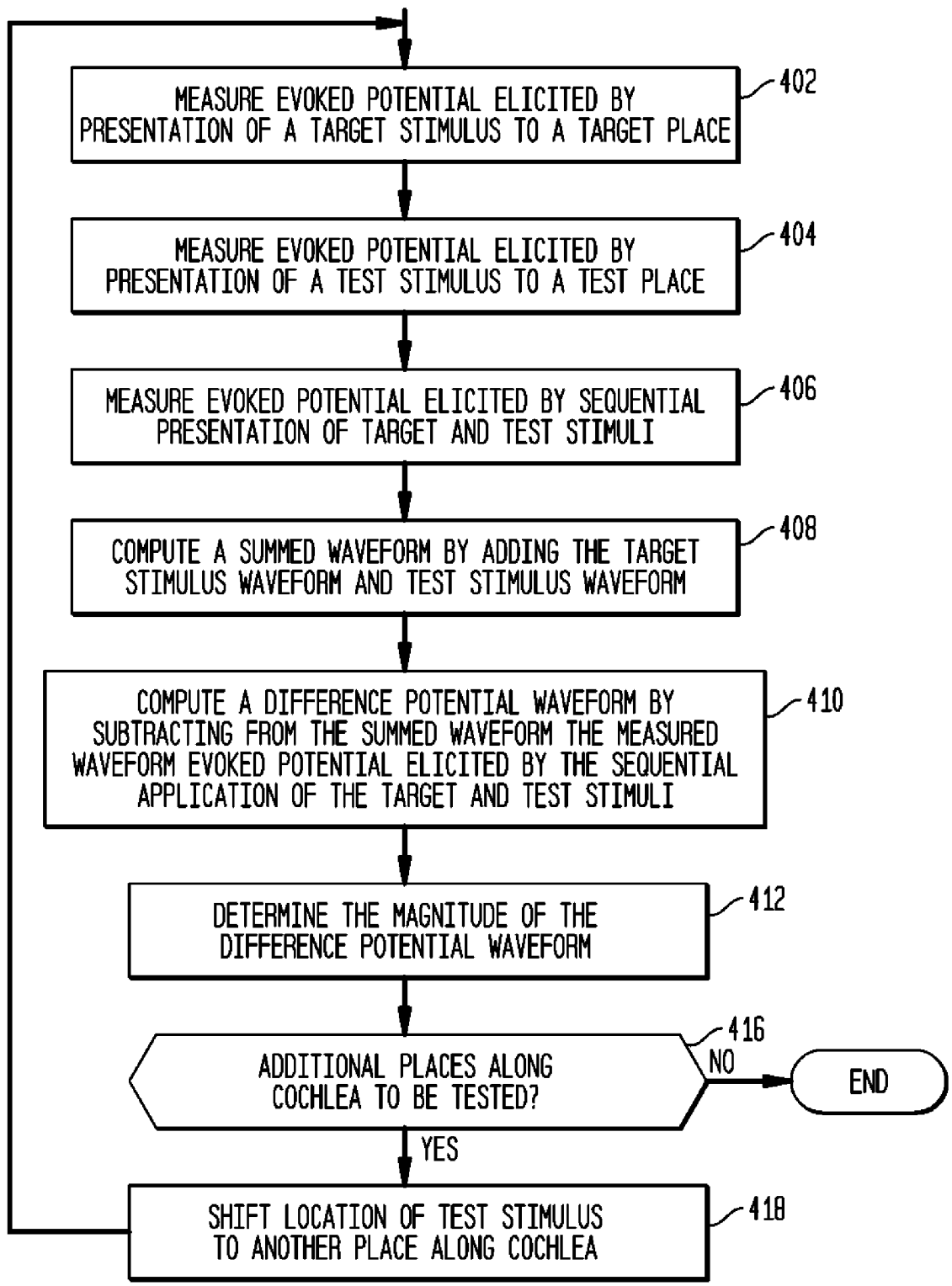
FIG. 4A is a flow diagram of one embodiment of the method of the invention.

The embodiment of FIG. 4A uses a focused test stimulus; the response is an evoked potential which is captured or recorded for later processing. Referring now to FIG. 4A, a flowchart of several steps of the method is illustrated. In the flowchart of FIG. 4A the several steps which are illustrated are executed in the order illustrated.

Figure 5A:
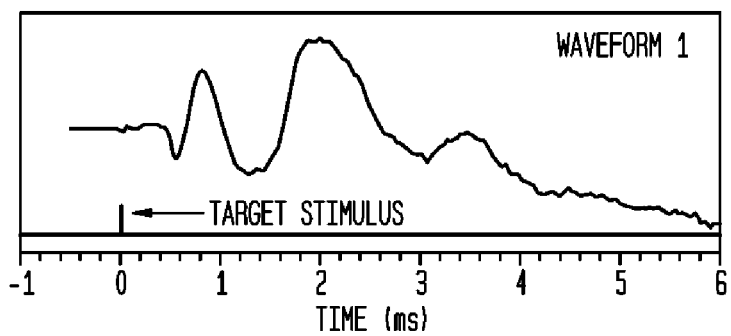
FIGS. 5A-5E are waveforms useful in describing the operation of the embodiment of FIG. 4A.

The first step 402 represents application of a target stimulus and the capture or measurement of an evoked potential which is the result of that stimulus. Typically, the target stimulus is not focused so it is applied at a single electrode of the array 134. In a preferred embodiment the target stimulus used in step 402 is a biphasic current pulse of duration 100 µsec/phase. FIG. 5A is an example which schematically illustrates the target stimulus (pointed to by the arrow in FIG. 5A) and the resulting evoked potential (identified as waveform 1). Often, if the signal is weak such as with an EABR, the waveform is measured using signal averaging. That is the stimulus is applied repeatedly, and the averaged response is computed to reduce noise in the signal.

Figure 5B:
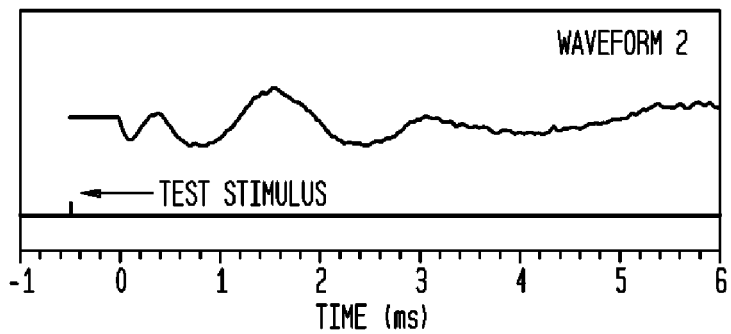

Step 404 represents the application of a test stimulus to the array 134 and the measurement and/or capture of an evoked potential in response to the test stimulus. In a preferred embodiment the test stimulus used in step 404 is a biphasic current pulse of duration 100 µsec/phase. As has been noted, the test stimulus is preferably focused, i.e., applied to more than a single electrode of the array 134 and up to and including all the electrodes of the array. In a preferred embodiment, the test stimulus is a phased array resulting from application of energy to each electrode in the array 134 producing constructive and destructive interference. FIG. 5B schematically illustrates the test stimulus (pointed to by the arrow), and the resulting evoked potential, waveform 2.

Figure 5C:
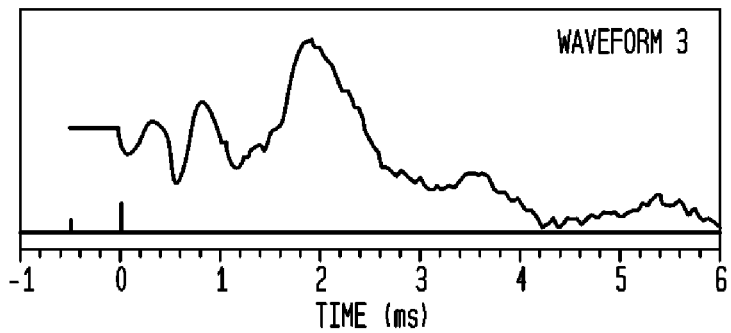

The next step, 406, represents the application of a sequence of a target and test stimuli (each preferably identical to the target and test stimulus already described) and the measurement and/or capture of the evoked potential in response to the sequence of stimuli. The response waveform associated with step 406 is shown in FIG. 5C (waveform 3). Firstly, note that in this embodiment the test stimulus application precedes that of the target stimulus. In a preferred embodiment the delay between the application of the test and target stimulus is 0.5 msec. In other embodiments the delay may be as small as zero. In still other embodiments of the invention, the test stimulus may follow the target stimulus. The response to the sequence of stimuli is illustrated in FIG. 5C and is labeled waveform 3.

Figure 5D:
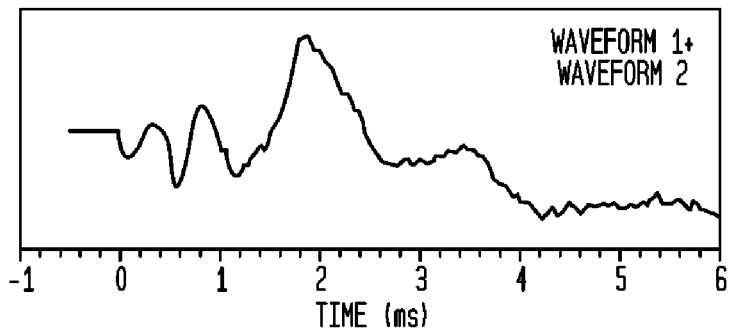

The next step 408 computes a summed waveform by summing waveform 1 and waveform 2. Note that FIGS. 5A and 5B have been temporally arranged so that the time delay between the test stimulus (FIG. 5B) and the target stimulus (FIG. 5A) is identical to the temporal sequence of the stimuli used in step 406. FIG. 5D shows the result of summing waveform 1 and waveform 2 (indicated as waveform 1+waveform 2).

Figure 5E:
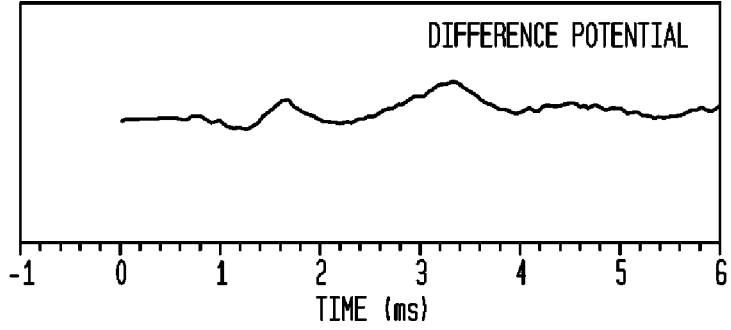

Step 410 computes a difference potential by subtracting from the summed waveform (that shown in FIG. 5D) the waveform produced in step 406-FIG. 5C. The result of the difference procedure is illustrated in FIG. 5E. FIG. 5E represents the difference potential produced by step 410. The magnitude of the difference potential represents the interaction of the stimuli on the assumption that if there were no interaction the magnitude of the difference potential would be null.

Step 412 determines the magnitude of the difference potential. A detail of step 412 is shown in FIG. 4B. As will be described the difference potential is processed to obtain a scalar value. This scalar value represents the interaction between the target and test stimuli based on the magnitude of the difference potential waveform, e.g., the waveform of FIG. 5E. Suffice it to say, at this point, the result of step 412 is a scalar value for the interaction between the target stimulus applied at a particular location in the array 134 and a test stimulus focused on a particular portion of the array 134. This value is one element of a profile of the array 134. The profile is developed by traversing the loop of steps 402-416 with a test stimulus focused at different locations, and preferably at each available location.

Figure 6:
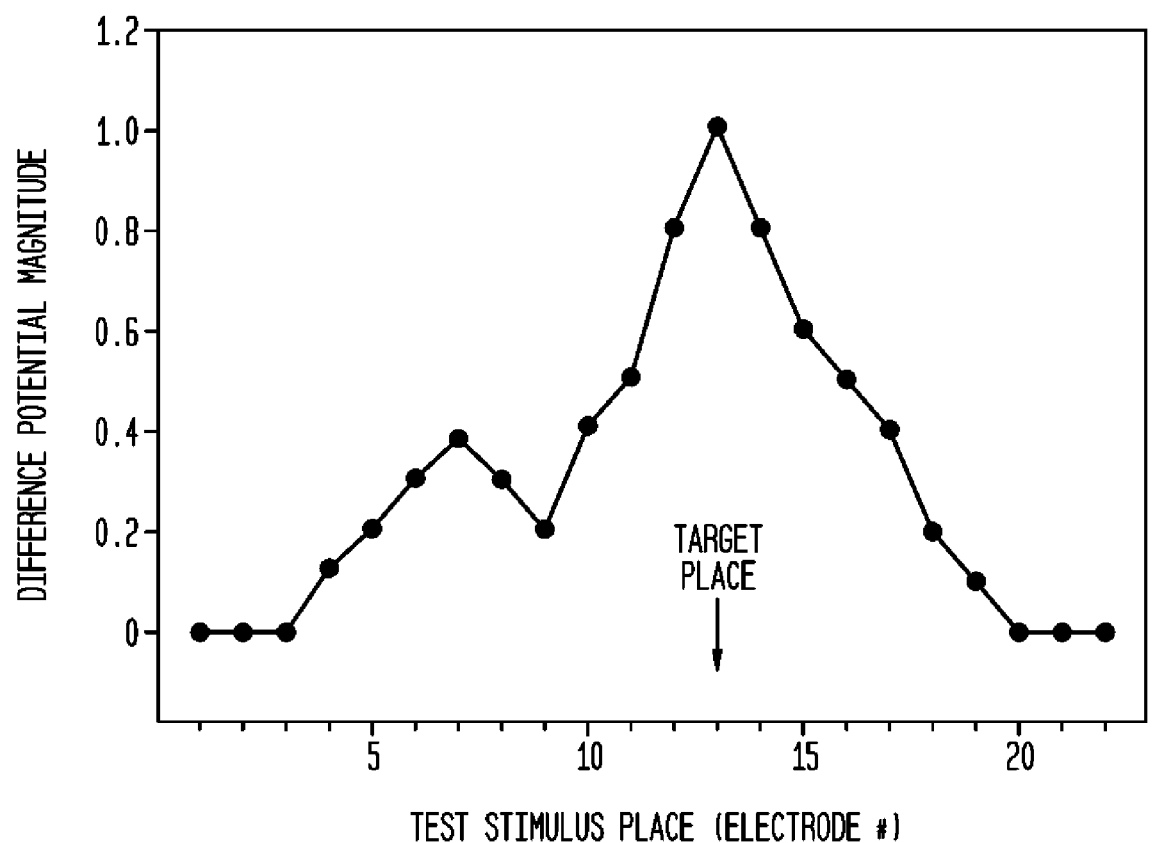
FIG. 6 is a plot of difference potential magnitude vs. test stimulus application location, e.g., a profile of interaction between target and test stimulus as a function of implant array location.

FIG. 6 shows the resulting profile. As noted, a single iteration of the steps of FIG. 4A quantifies the resulting waveform to produce a scalar value (one point on the curve of FIG. 6). The location of the test stimulus (the electrode in the array at which the test stimulus is focused) is plotted on the abscissa and the difference potential magnitude is plotted on the ordinate. The scale of the abscissa shown in FIG. 6 is electrode number where the highest number represents apical electrode of the array. Other points in the curve are produced by changing the focal point of the test stimulus from electrode to electrode along the array. The result is a profile of the interaction between the test stimulus and target stimulus for the given location of the target stimulus. The peak of the curve of FIG. 6 occurs at electrode 13 which is the location of the application of the target stimulus. The dip in excitation at electrode 9 indicates that fewer neurons respond to the target stimulus at this place. This may be due to a relative paucity of surviving neurons at this place or a relatively weak electrical stimulus field at this location.

FIG. 4B is a detail of step 412 of FIG. 4A. As shown in FIG. 4B, a first step 452 operates on the difference potential waveform and effects two functions. Firstly, step 452 provides for artifact removal and, secondly, the step provides for band pass filtering. Artifact removal may be automatic. Artifacts are a brief but large transient disturbance in the recorded electrical signal caused by the stimulating current pulse. The most common method of artifact removal is to simply to blank the signal during the pulse by forcing it to zero volts or some fixed value. This may also be done in software after digitization. Neural signals generally have energy between about 1 and 3 kHz. Energy outside this spectral region is presumably of nonneural origin, such as thermal noise. Thus, a typical bandpass would generally pass the range of about 1 to 3 kHz.

Step 454 operates on the result of the process of step 452 to first determine the mean e.g. a DC value and then subtract the mean from the processed waveform of step 452. Finally, step 456 operates on the result of the process of step 454 to compute the Root Mean Square (rms) value of the resulting signal. The rms value is a scalar which represents the interaction of the test and target stimulus for the location at which the test stimulus is focused.

Figure 3A:
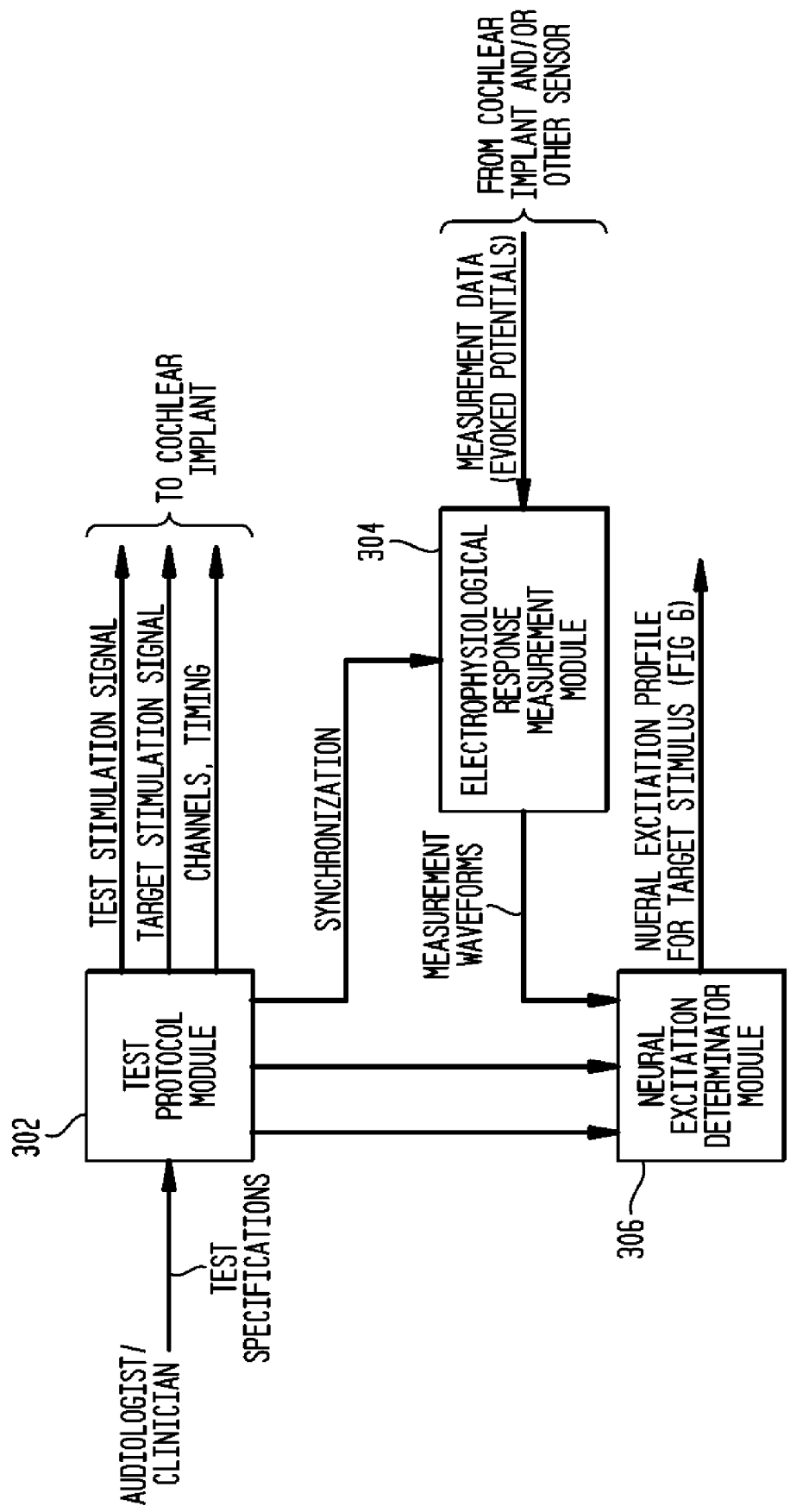
FIG. 3A is a functional block diagram of apparatus capable of implementing the invention.

FIG. 3A is a functional block diagram of an apparatus which is capable of implementing the steps of the invention illustrated in FIG. 4A. The apparatus includes a test protocol module 302, electrophysiological response measurement module 304 and a neural excitation determinator module 306. The audiologist/clinician inputs test specifications to the test protocol module 302. Test specifications include, the intensity of the test and target stimulus, the technique used for focusing the test stimulus, the sequence of the target/test stimulus to be used in step 406, the delay between the components of the sequence, etc. The test specifications describe the format and intensity of the test and target stimulus, the range over which the test stimulus is focused, i.e., initial focus location, next focus location, etc. the various locations given in terms of electrode location within the array. The detailed specifications for the focusing of the test stimulus (phased array, or other type of focusing, etc.) may or may not be under the control of the audiologist. The test protocol module 302, when initiated into operation by the audiologist/clinician provides a trio of signals to the implant 134. These signals include the test stimulus signal, the target stimulus signal, and information respecting the channels (electrode or electrodes) and timing of the signals (order, duration and delay). The test protocol module 302 also provides synchronization information to an electrophysiological response measurement module 304 and to the neural excitation determinator module 306. The synchronization information allows the electrophysiological response measurement module 304 to classify the measurement data, e.g. the evoked potentials which are received from the cochlear implant and/or other sensor. Using the synchronization information from the test protocol module 302, electrophysiological response measurement module 304 may categorize the received evoked potential as the evoked potential in response to a test stimulus or the evoked potential in response to a target stimulus, or the evoked potential in response to the sequence of test and target stimuli. Electrophysiological response measurement module 304 with information as to the exact identity of the evoked potential may appropriately record and/or measure the evoked potential which is input from the cochlear implant and/or other sensor. The neural excitation determinator module 306 receives inputs from both the electrophysiological response measurement module 304 and the test protocol module 302. The neural excitation determinator module 306 implements the computations required in the flow chart of FIG. 4A. In particular, the neural excitation determinator module 306 must compute the summed waveform (step 408); it must compute a difference potential waveform (step 410), and then it must determine the magnitude of a difference potential waveform. With the respective waveforms available to the neural excitation determinator module 306 from the electrophysiological response measurement module 304, and information from the test protocol module 302 on the identity of the particular waveforms presented, the neural excitation determinator module 306 may make these two computations and then the determination. This process provides for a single point of the profile shown in FIG. 6. The neural excitation determinator module 306 then repeats this process for each other location at which the test stimulus is focused. After treating each of the other locations at which the test stimulus is focused, the neural excitation determinator module 306 will have produced the plot of FIG. 6, or the profile. That information then is output from the module 306.

Figure 3B:
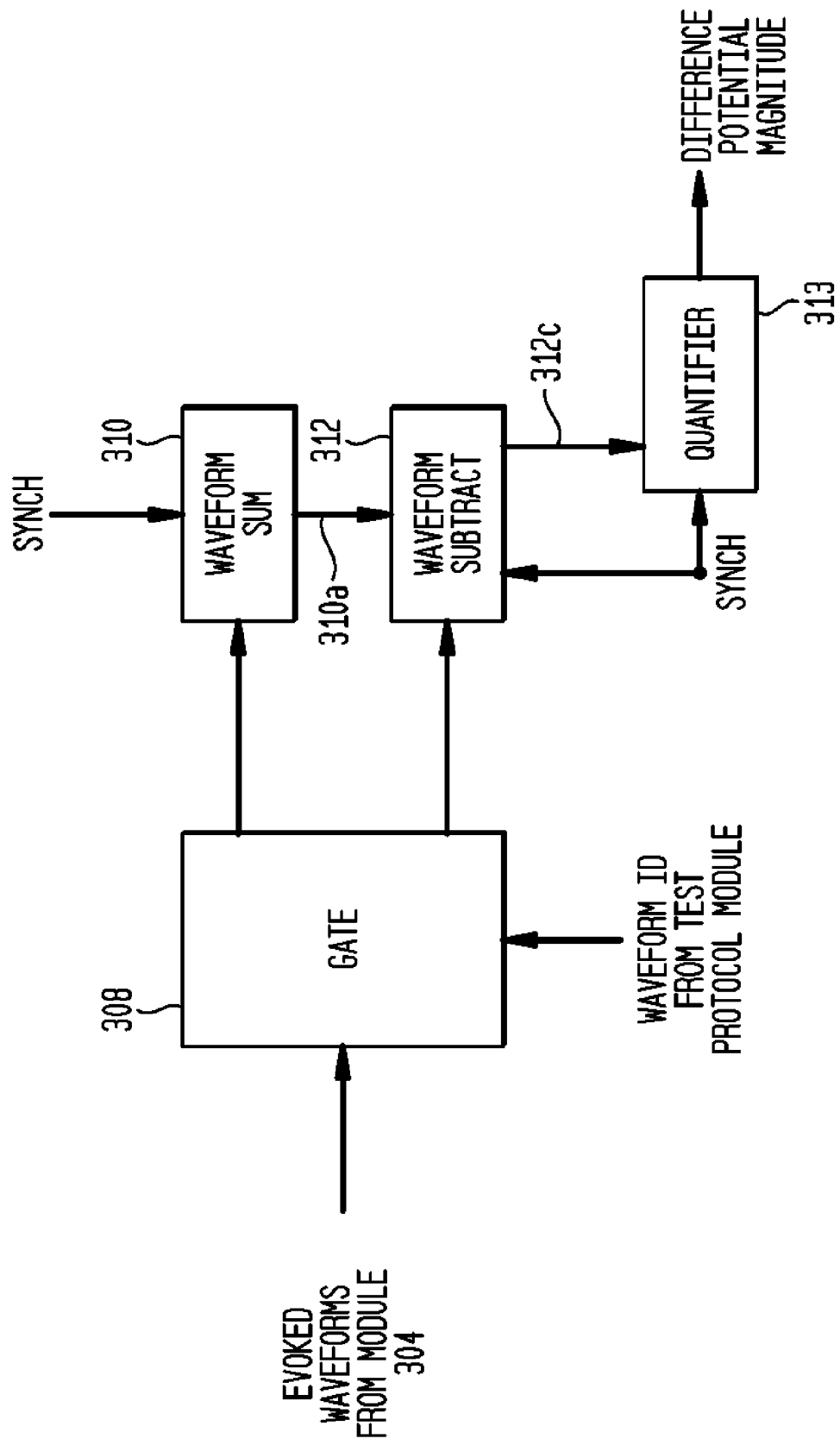
FIG. 3B is a detail of the neural excitation module 306 of FIG. 3A.

FIG. 3B is a detail of the neural excitation determinator module 306. As shown in FIG. 3B, the neural excitation determinator module receives (in seriatim) on one input terminal the three evoked potentials, particularly the evoked potential in response to the test stimulus, the evoked potential in response to the target stimulus and the evoked potential in response to the sequence. These inputs are provided in time sequence (as they are generated) to gate 308. Gate 308 directs the first two evoked responses which are responses to the target and test stimulus responses, respectively, to the waveform sum device 310. Since the evoked responses due to the test and target stimulus are not synchronous, the waveform sum device 310 includes a memory to bring the two waveforms into time synchronization so they may be summed. The waveform sum device 310 produces at its output 310a the waveform of FIG. 5D (the sum of waveforms 1 and 2). The output of the waveform sum device 310 is provided as one input to the waveform subtraction device 312. The other input to the waveform subtraction device is the evoked potential in response to the sequence of test and target stimuli applied in step 406. This input to the waveform subtract device 312 is provided from the gate 308 which directs this waveform to the waveform subtract device 312 as that waveform is identified to the gate 308 from the test protocol module 302. The output of the waveform subtract device 312 on its output 312a corresponds to the difference potential, the waveform of FIG. 5E. This waveform is input to the quantifier 313 which performs the functions shown in FIG. 4B to produce a difference potential magnitude. A different difference potential magnitude is provided for each different location at which a test stimulus is focused. The collection of the difference potential magnitude taken together with the identification of the focus location constitutes the profile of FIG. 6

The preceding embodiments employ an evoked potential. The following embodiments are based on the recipient's perception.

A forward or simultaneous masking paradigm may be used to measure interaction between the target and test stimuli. FIG. 4C shows another embodiment which is based on recipient perception. The stimuli are repeated bursts of biphasic pulses, repeated sufficiently long to be perceived. Step 480 provides a test (focused) stimulus repeated at increasing intensities, beginning at a stimulation intensity which is not perceptible to the recipient. As the intensity is increased the recipient signals a transition from a not perceptible state to the perceptible stimulus domain. The recipient may signal this transition in any of many ways such as pressing a button or closing a switch which is wired to the programming system 142 allowing that equipment to capture or record the magnitude of stimulus at the threshold. Alternatively the recipient may signal the audiologist or clinician. In this case it is the audiologist or clinician who implements a capture or record of the threshold intensity. This minimum intensity which is perceptible is termed the "unmasked threshold".

The unmasked threshold may be measured by any of a set of well known procedures including:
 a. Method of Adjustment
 b. Method of Constant Stimuli
 c. Adaptive Procedure
 d. Bekesy Tracking
 e. Counted Ts.

In step 482 a sequence of stimuli is presented (each of the form already described). First the target stimulus is presented as an unfocused stimulus at a fixed intensity (judiciously chosen). The target stimulus may be referred to as the "masker." The test stimulus (probe) follows, either directly or after a brief delay such as 20 msec. or less. The test stimulus (probe) is focused. This sequence is presented repeatedly as the intensity of the probe is varied. The iterations begin at a probe intensity which is not perceptible. The probe intensity is increased until the recipient signals the probe is perceptible. This is termed the "masked threshold". The masked threshold may be captured or recorded in the same fashion as the unmasked threshold was captured or recorded.

As shown in FIG. 4C at step 484 a difference is computed between the unmasked and masked thresholds. This difference represents the interaction of the stimuli for the location of the focused probe. The location of the probe is then shifted along the electrode array and the steps 480-486 are repeated. This is implemented, after executing step 484, by testing (step 488) whether there are additional places to be tested. Processing loops back to step 480 with the probe focused at the new place (step 490). This looping is repeated until there are no new places, in which event the processing "ends". This procedure develops a difference corresponding to each electrode location in the array. When plotted the several differences produce a profile as shown in FIG. 6.

Various alternatives are possible. In one alternative the test stimulus (focused stimulus) serves as the masker (the leading component of the sequence of step 482) and the target (unfocused stimulation) serves as the probe. The intensity of the (test stimulus) masker is adjusted to achieve a criterion probability of probe detection. Interaction is quantified by the inverse of the adjusted Masker intensity. In another similar alternative the target stimulation is focused too.

The first embodiment employed an evoked potential as the response. One variation is to use the compound action potential (CAP) of the auditory nerve as the response measure.

As a further alternative a middle-latency or cortical response from the auditory central nervous system may be substituted as a response measure.

Instead of quantifying the magnitude of the difference potential, the magnitude of each waveform may be computed (using the procedure of FIG. 4B), and interaction determined from the difference between the magnitude of waveform 3 (the response to the sequence) and that of the summed waveform.

As a further alternative the focusing of the test stimulus need not employ a phased array stimulus. Instead suboptimal stimulus focusing may be used. In particular, a limited phased array stimulus (using fewer than all available electrodes or imperfect weighs) may provide sufficient focusing, including a set of only three electrodes. Simple symmetric quadrupolar or tripolar stimuli may also provide sufficient focusing for a useful implementation.

The foregoing portion of the specification describes several embodiments of the invention wherein neural excitation is assessed by applying stimuli using the apparatus illustrated in FIG. 1 which is controlled and responses sensed by the apparatus of FIG. 2, including the programming system 142. The programming system 142 may be implemented with commercially available desk top or lap top computers along with an interface to the implant illustrated in FIG. 1. The application of the stimulus may be manually controlled by the audiologist or clinician using the programming system 142. Alternatively the audiologist or clinician, having determined of confirmed that stimulus parameters stored in the programming system 142 are appropriate, may merely initiate the automatic application of the stimuli with the parameters already described. The programming system 142 may also then capture or record the responses whether evoked or perceptual. Evoked or other electrically manifested responses may be captured via the interface already mentioned. Perceptual responses may also be electrically manifested and captured via the same interface so long as the recipient has access to suitable circuits with buttons or switches with which to manifest the appropriate response. Thus the programming system 142 may automatically implement the assessment methods described above controlled by computer readable media having recorded thereon instructions which, when executed by the computer implements the methods already described.

Further features and embodiments of the present invention may be described in U.S. Provisional Application No. 60/949,682, entitled "USE OF FOCUSED STIMULI TO MEASURE A NEURAL EXCITATION PROFILE WITHIN THE COCHLEA," filed Jul. 13, 2007; U.S. Provisional Application No. 60/949,647 entitled "USE OF FOCUSED STIMULI TO MEASURE A NEURAL EXCITATION PROFILE WITHIN THE COCHLEA," filed Jul. 13, 2007; and U.S. Utility Application entitled "ASSESSING NEURAL SURVIVAL," filed Jul. 14, 2008 which are all hereby incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A method of assessing neural excitation using interaction between two stimuli, wherein both stimuli are applied by at least one electrode of an electrode array, said method comprising:
    applying a first stimulus;
    capturing a response to said first stimulus;
    applying a second stimulus in timed relation to application of said first stimulus;
    capturing a response to said second stimulus; and
    determining neural excitation from said captured responses,
    wherein at least one of said first and second stimulus is focused.

2. A method as recited in claim 1 wherein the second stimulus is applied within about 20 ms or less after application of the first stimulus.

3. A method of obtaining an interaction profile which comprises iteratively executing a method as recited in claim 2, in which a locus of application of said focused stimulus is changed on different iterations of the method of claim 2.

4. A method as recited in claim 3 wherein the stimuli are applied to a cochlea.

5. A method as recited in claim 4 wherein said response is an evoked potential.

6. A method as recited in claim 4 wherein said focused stimulus is focused employing constructive and destructive interference resulting from application of energy to plural electrodes of said array.

7. A method as recited in claim 4 wherein each said stimuli is a biphasic current pulse of about 100 μs per phase.

8. A method as recited in claim 7 wherein said response is an Electrical Auditory Brainstem Response (EABR).

9. A method as recited in claim 7 wherein said response is a compound action potential (CAP).

10. A method as recited in claim 1 wherein said focused stimulus is focused with a phased array wherein each electrode of said array is energized.

11. A method of assessing neural excitation by a given stimulus by measuring a response to interaction of two stimuli, including said given stimulus, each stimulus applied to at least one electrode in an array, said method comprising:
    applying a first stimulus to at least one electrode of said array;
    capturing a first response to application of said first stimulus;
    applying a second stimulus including:
        energizing at least two electrodes of said array using constructive and destructive interference so as to form said second stimulus as a focused stimulus;
    capturing a second response to application of said second stimulus;
    capturing a third response to a sequence of the second stimulus followed, after a given delay, by the first stimulus;
    determining a computed response by summing said first and second responses, temporally adjusted to exhibit a delay equivalent to said given delay; and
    determining a difference response by obtaining a difference between said computed response and said third response.

12. The method of claim 11 wherein said first stimulus is unfocused.

13. A method for determining a plurality of difference potentials comprising a response profile, wherein said method comprises:
    iteratively obtaining a response as recited in claim 12, on each iteration of determining a difference potential as recited in claim 12; and
    applying said focused stimulus at a location which differs from other applications of said focused stimulus.

14. A method as recited in claim 13 wherein said first stimulus is unfocused.

15. A method as recited in claim 14 wherein said first and second stimulus each comprise a biphasic current pulse of approximately 100 μs/phase.

16. A method as recited in claim 15 wherein said given delay is approximately 0.5 ms.

17. A method as recited in claim 13 wherein said first and second stimulus each comprise a biphasic current pulse of approximately 100 μs/phase.

18. A method as recited in claim 17 wherein said given delay is approximately 0.5 ms.

19. The method of claim 11 wherein said focused stimulus employs a phased array wherein energy is applied to each electrode of said array.

20. The method of claim 11 wherein said response is an evoked potential.

21. The method of claim 20 wherein said evoked potential is an Electrical Auditory Brainstem Response (EABR).

22. The method of claim 11 wherein said response is a compound action potential.

23. The method of claim 11 which further comprises:
    quantifying said difference response by determining a mean;
    producing a result by subtracting said mean from said difference response; and computing a root means square value (rms) of said result where said quantifying uses said rms value to quantify said difference response.

24. A non-transitory computer readable medium supporting a series of instructions which when executed implement a method of assessing neural excitation by a given stimulus by measuring a response to interaction of two stimuli, including said given stimulus, each stimulus applied to at least one electrode in an array, said method comprising:
- applying a first stimulus to at least one electrode of said array;
- capturing a first response to application of said first stimulus;
- applying a second stimulus including:
  - energizing at least two electrodes of said array using constructive and destructive interference so as to form said second stimulus as a focused stimulus;
- capturing a second response to application of said second stimulus;
- capturing a third response to a sequence of the second stimulus followed, after a given delay, by the first stimulus;
- determining a computed response by summing said first and second responses, temporally adjusted to exhibit a delay equivalent to said given delay; and
- determining a difference response by obtaining a difference between said computed response and said third response.

25. The computer readable medium of claim 24 wherein the method further comprises:
- quantifying said difference response by determining a mean;
- producing a result by subtracting said mean from said difference response; and
- computing a root means square value (rms) of said result where said quantifying uses said rms value to quantify said difference response.

* * * * *